(12) United States Patent
Tsoneva et al.

(10) Patent No.: US 12,138,066 B2
(45) Date of Patent: Nov. 12, 2024

(54) METHOD AND SYSTEM FOR DELIVERING SENSORY SIMULATION BASED ON EVOKED RESPONSE QUANTIFICATION

(71) Applicant: KONINKLIJKE PHILIPS N.V., Eindhoven (NL)

(72) Inventors: Tsvetomira Kirova Tsoneva, Eindhoven (NL); Gary Nelson Garcia Molina, Madison, WI (US); Stefan Pfundtner, Eindhoven (NL); Sander Theodoor Pastoor, Vleuten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 694 days.

(21) Appl. No.: 16/832,881

(22) Filed: Mar. 27, 2020

(65) Prior Publication Data

US 2020/0305753 A1    Oct. 1, 2020

Related U.S. Application Data

(60) Provisional application No. 62/826,135, filed on Mar. 29, 2019.

(51) Int. Cl.
*A61B 5/377* (2021.01)
*A61B 5/00* (2006.01)
(Continued)

(52) U.S. Cl.
CPC .............. *A61B 5/377* (2021.01); *A61B 5/378* (2021.01); *A61B 5/38* (2021.01); *A61B 5/381* (2021.01); *A61B 5/4812* (2013.01)

(58) Field of Classification Search
CPC ... A61B 5/0006; A61B 5/0022; A61B 5/0205; A61B 5/377; A61B 5/378; A61B 5/38;
(Continued)

(56) References Cited

U.S. PATENT DOCUMENTS

2013/0303837 A1*  11/2013  Berka .................... A61B 5/389
                                                                      600/27
2015/0306391 A1*  10/2015  Wu ....................... A61N 1/36078
                                                                      607/45
(Continued)

FOREIGN PATENT DOCUMENTS

WO    WO-2017109621 A1 *  6/2017  ........... A61B 5/0478
WO    WO-2019018400 A1 *  1/2019  ......... A61B 5/02108

OTHER PUBLICATIONS

Osterhout, L. (Nov. 14, 2007). ERP Tutorial. Cognitive Neuroscience of Language Lab. Retrieved Jun. 16, 2022, from https://web.archive.org/web/20071114200036/http://faculty.washington.edu/losterho/erp_tutorial.htm (Year: 2007).*

(Continued)

*Primary Examiner* — Christine H Matthews
*Assistant Examiner* — Marc D. Honrath

(57) ABSTRACT

A system for delivering sensory stimulation a sensor; a sensory stimulator configured to deliver sensory stimulation to a patient during a sleep session, the sensory stimulation having varying stimulation intensity levels; and a computer system. One or more physical processors being programmed with computer program instructions which, when executed cause the computer system to: determine sleep stage information of the patient based on brain activity information of the patient during the sleep session from the sensor; provide input to the sensory stimulator based on the determined sleep stage information of the patient, the provided input causing the sensory stimulator to deliver the sensory stimulation to the patient; obtain stimulation response information from the patient, the stimulation response information including patient brain response to the delivered sensory stimulation; and determine a range of the stimulation inten-
(Continued)

sity levels within which the patient brain response reaches a threshold.

9 Claims, 12 Drawing Sheets

(51) Int. Cl.
    *A61B 5/378*     (2021.01)
    *A61B 5/38*     (2021.01)
    *A61B 5/381*     (2021.01)

(58) Field of Classification Search
CPC ..... A61B 5/381; A61B 5/4806; A61B 5/4812; A61B 5/7264; A61M 2021/0016; A61M 2021/0022; A61M 2021/0027; A61M 2021/0044; A61M 2021/0055; A61M 2021/0072; A61M 21/02; A61M 21/3553; A61M 21/3569; A61M 21/3584; A61M 21/3592; A61M 21/505; A61M 2209/088; A61M 2210/0662; A61M 2230/06; A61M 2230/10; A61M 2230/40; A61M 2230/63; A61N 1/36031; A61N 2/006; A61N 2/02; A61N 2005/0626; A61N 5/0622; G16H 20/30
See application file for complete search history.

(56) References Cited

U.S. PATENT DOCUMENTS

2016/0058970 A1* 3/2016 Garcia Molina .... A61B 5/4812 600/27
2016/0302718 A1* 10/2016 Laura Lapoint ....... A61B 5/375
2017/0000970 A1* 1/2017 Garcia Molina ..... A61M 21/02
2017/0340854 A1* 11/2017 Geerlings ............ A61B 5/4812

OTHER PUBLICATIONS

Lopez-Calderon, J., & Luck, S. J. (2014). ERPLAB: An open-source toolbox for the analysis of event-related potentials. Frontiers in Human Neuroscience, 8. https://doi.org/10.3389/fnhum.2014.00213 (Year: 2014).*
International Search Report and Written Opinion Dated Jun. 7, 2020 From Corresponding PCT Application No. PCT/EP2020/058846 Filed Mar. 27, 2020.
Anonymous, "SIGGI II: Signal Generator & Impedance Meter", Brain Vision UK, http://brainvision.co.uk/easycap-siggi-ii.
Tononi, G. and Cirelli, C. Feb. 2006. Sleep function and synaptic homeostasis. Sleep Med. Rev. 10, 49-62.
Riedner, B. A., Hulse, B. K., Ferrarelli, F., Sarasso, S., Tononi, G. 2010. Enhancing sleep slow waves with natural stimuli, Medicamundi. 45, 82-88.
Regan, D., 1989. Human brain electrophysiology: evoked potentials and evoked magnetic fields in science and medicine.
Atienza, M., Cantero, J.L., Escera, C., 2001. Auditory information processing during human sleep as revealed by event-related brain potentials. Clin. Neurophysiol. 112, 2031-2045.
Pfurtscheller, G., Lopes, F.H., 1999. Event-related EEG / MEG synchronization and desynchronization: basic principles. Clin. Neurophysiol. 110, 1842-1857.
Bastuji, H., Garcia-Larrea, L., 1999. Evoked potentials as a tool for the investigation of human sleep. Sleep Med. Rev. 3, 23-45.
Pfurtscheller, G., Neuper, C., Mohl, W., 1994. Event-related desynchronization (ERD) during visual processing. Int. J. Psychophysiol. 760.
Andreassi, J.L., 2013. Psychophysiology: Human behavior & physiological response. Psychology Press.

* cited by examiner

METHOD AND SYSTEM FOR DELIVERING SENSORY SIMULATION BASED ON EVOKED RESPONSE QUANTIFICATION

CROSS-REFERENCE TO PRIOR APPLICATIONS

This application claims the benefit of U.S. Provisional Application No. 62/826,135, filed on 29 Mar. 2019. This application is hereby incorporated by reference herein.

BACKGROUND

1. Field

The present disclosure pertains to a method and a system for delivering sensory stimulation to a patient, specifically, a method and a system for automatically adjusting a simulation intensity range of sensory stimulation during sleep based on evoked response quantification.

2. Description of the Related Art

Sleep is a reversible state of disconnection from the external environment, characterized by quiescence and reduced vigilance. The state of the brain and body are not uniform throughout a complete night of sleep, a fact that many believe means that sleep has multiple purposes.

Normal sleep is characterized by sleep stages which occur in a cyclic manner (sleep cycles) and have a different contribution to the restorative value of sleep. Five sleep stages can be identified with polysomnography (PSG). Stage 1 and 2 are the stages of light sleep, characterized by theta (4-8 Hz) oscillatory brain activity, and sleep spindles and K-complexes respectively. Stage 3, and formerly also stage 4, are the stages of deep sleep characterized with slow-waves and delta activity (0.5-4 Hz). Rapid-Eye Movement (REM) sleep typically occurs after around 90 minutes of sleep onset and is characterized by increased eye movement, hearth rate, and respiration.

Systems for monitoring sleep are known. Known systems detect sleep stages in a subject during a sleep session. The detected sleep stages include stages that correspond to slow wave sleep. Typically, slow wave sleep is detected based on fixed slow wave detection parameters.

Recent results have shown that peripheral (e.g. electric, magnetic, or sensory) stimulation during deep sleep (stages 3 and 4) can enhance slow-wave activity and increase the restorative value of sleep. The sensory stimulation is delivered in a closed loop manner by: monitoring the user's electroencephalogram (EEG) during sleep; identifying appropriate moments for stimulation and delivering auditory stimulation to enhance sleep slow waves without causing arousals.

The high time resolution of scalp recorded EEG data/information provides a good basis for studying the brain responses to external or internal events. Such events elicit a stereotypical brain response, time and phase locked to event onset, known as event related potential (ERP). The ERPs are voltage fluctuations arising from summed postsynaptic potentials of large neural populations firing synchronously during processing of information. The ERPs are calculated as the average waveform over a number of events and the amplitude and latency of the successive peaks in the ERP waveform can be used to determine the time course of information processing in the brain. Auditory evoked ERP suffer progressive amplitude decrease and latency increase from wakefulness to sleep stage 3 of slow wave sleep (SWS), but they can surpass waking values during rapid-eye movement (REM) sleep.

Alternatively, EEG can also reveal the functional role and the interaction between the different oscillatory systems involved in various mental states and processes. Frequency specific changes of the ongoing EEG activity reflect the decrease or increase in synchrony of the underlying neuronal populations and manifest as decreases or increases of power in specific EEG frequency bands. When those changes are time-locked to a specific event they are called the event-related desynchronization (ERD) or synchronization (ERS). The event-related desynchronization (ERD) represents an amplitude decrease of rhythmic activity, while the event-related synchronization (ERS) represents an amplitude increase.

The effect of sensory stimulation during sleep depends on a number of factors. These factors include stimulation intensity, stimulation timing within the sleep cycle, the ongoing slow waves phase, depth of sleep, and subject's age/gender. When it comes to auditory stimulation, the volume is one of the factors that play a major role. Too low volumes would not reach the sleeping brain which is wired to block out irrelevant stimuli, while too high volumes could cause conscious perception and lead to awakening.

Different intensity modulation strategies are possible, e.g., titrating the stimulus intensity in a progressively increasing manner; or making the intensity dependent on an estimation of sleep depth. In all cases, however, to deliver effective stimulation without causing arousals, the intensity is modulated within a predefined range defining the upper and lower intensity limits. These limits can be subjectively determined for each user through perceptual tests.

The lower limit could be set to the perceptual sensitivity threshold (e.g., lowest tone volume perceived by the user). To set the upper limit, each user can be presented with stimuli with progressively increasing intensity and then asked to estimate the intensity they think could wake them up. This method, however, is quite laborious and not very intuitive as subjects have little insight about the maximum intensity they can tolerate during sleep without being awoken.

Stimulation of increasing stimulation intensity produces reliable increase in the event related potential (ERP) amplitude. In the case of auditory stimulation, the stimulation is the volume. FIG. 1 shows this amplitude increase for an auditory evoked ERP with increasing tone volume during sleep stage 3 of a subject. The same phenomena can be observed across stimulation modalities also in the visual and somatosensory domain for both transient and steady-state responses. Similarly, event-related changes in spectral power (e.g., event-related desynchronization (ERD) or synchronization (ERS)) in different frequency bands are also sensitive to stimulus intensity. The graph of FIG. 1 shows amplitude (measured in microvolts) on the Y-axis. Time is on the X-axis of the graph of FIG. 1 and is measured in microseconds.

Referring to FIG. 1, curve A (i.e., at 0 dB) is essentially flat and portrayed here as baseline reference. Curves B and C in FIG. 1 correspond to 39 and 43 dB, respectively. As shown in FIG. 1, the curve C (i.e., 43 dB) clearly leads to the highest ERP amplitude. While the shape of the response changes from wakefulness to sleep, due to the interplay of other protective mechanisms in the human brain during sleep (such as the generation of K-complexes and sleep spindles), the response amplitude attenuation or the complete absence of response are a clear indication of the stimuli salience. Additionally, the mechanisms serving deviance detection in non-REM sleep are reflected by progressive attenuation of the responses to repetitive stimuli (habituation), but recovery to a full-amplitude by sudden changes in stimulus characteristics. This supports the idea that the brain continues to process external events across all sleep stages with response amplitude characterizing stimuli relevance.

These EEG signatures can be used to identify if external stimulation has an effect on the brain. In the context of slow-wave sleep enhancement two questions often arise: 1) did the delivered stimulation actually reach the sensory systems of the brain? and 2) what is the optimal stimulation intensity (volume in the case of auditory stimulation) range given possible subject variability?

Individuals of different age, gender, sensitivity profile have different tolerance to sound, light or touch, different arousal threshold and different EEG range. Hence, if sensory stimulation is used to enhance sleep, individual differences need to be considered.

Furthermore, for devices that are used in the home setting, one has to deal with unavoidable misplacement of sensors and/or actuators, which might result in unperceived stimulation despite delivery. Realizing this is important for the correct estimation of various sleep parameters which are reported back to the user of such system.

Currently 30% of the sleep therapy delivered appear to be below general perceptual level. On top of that the inter-individual differences have to be added, which cause tones above general perceptual level that still do not produce any measurable effect in the EEG (i.e., possibly due to different hearing levels or differences in depth of sleep of the individuals). Then, on the other side, there is the problem of tone related arousals, which fragment the sleep and reduce the amount of stimulation that could be delivered in a night. All these contribute to the low slow wave activity enhancement in a number of individuals (e.g., 20% non-responders across studies).

SUMMARY

Accordingly, it is an object of one or more embodiments of the present patent application to provide a system for delivering sensory stimulation. The system comprises a sensor configured to measure brain activity information of a patient during a sleep session; a sensory stimulator configured to deliver sensory stimulation to the patient during the sleep session, the sensory stimulation having varying stimulation intensity levels; and a computer system. The computer system comprises one or more physical processors operatively connected with the sensor and the sensory stimulator. The one or more physical processors being programmed with computer program instructions which, when executed cause the computer system to: determine sleep stage information of the patient based on the brain activity information of the patient during the sleep session; provide input to the sensory stimulator based on the determined sleep stage information of the patient, the provided input causing the sensory stimulator to deliver the sensory stimulation to the patient; obtain stimulation response information from the patient, the stimulation response information including patient brain response to the delivered sensory stimulation; and determine a range of the stimulation intensity levels within which the patient brain response reaches a threshold.

It is yet another aspect of one or more embodiments of the present patent application to provide a method for delivering sensory stimulation. The method is implemented by a computer system comprising one or more physical processors executing computer program instructions that, when executed, perform the method. The method comprises determining, using the computer system, sleep stage information of a patient based on brain activity information of the patient during a sleep session, the brain activity information of the patient during the sleep session being measured by a sensor; providing input to a sensory stimulator based on the determined sleep stage information of the patient, the provided input causing the sensory stimulator to deliver the sensory stimulation to the patient, the sensory stimulation having varying stimulation intensity levels; obtaining stimulation response information from the patient, the stimulation response information including patient brain response to the delivered sensory stimulation; and determining, using the computer system, a range of the stimulation intensity levels within which the patient brain response reaches a threshold.

It is yet another aspect of one or more embodiments to provide a system for delivering sensory stimulation. The system comprises a means for measuring brain activity information of a patient during a sleep session; a means for delivering sensory stimulation to the patient during the sleep session, the sensory stimulation having varying stimulation intensity levels; and a means for executing machine-readable instructions with at least one processor, wherein the machine-readable instructions comprising: determining sleep stage information of the patient based on the brain activity information of the patient during the sleep session; providing input to the means for delivering based on the determined sleep stage information of the patient, the provided input causing the means for delivering to deliver the sensory stimulation to the patient, the means for delivering having varying stimulation intensity levels; obtaining stimulation response information from the patient, the stimulation response information including patient brain response to the delivered sensory stimulation; and determining a range of the stimulation intensity levels within which the patient brain response reaches a threshold.

These and other objects, features, and characteristics of the present patent application, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present patent application.

DETAILED DESCRIPTION OF EXEMPLARY EMBODIMENTS

Figure 1:
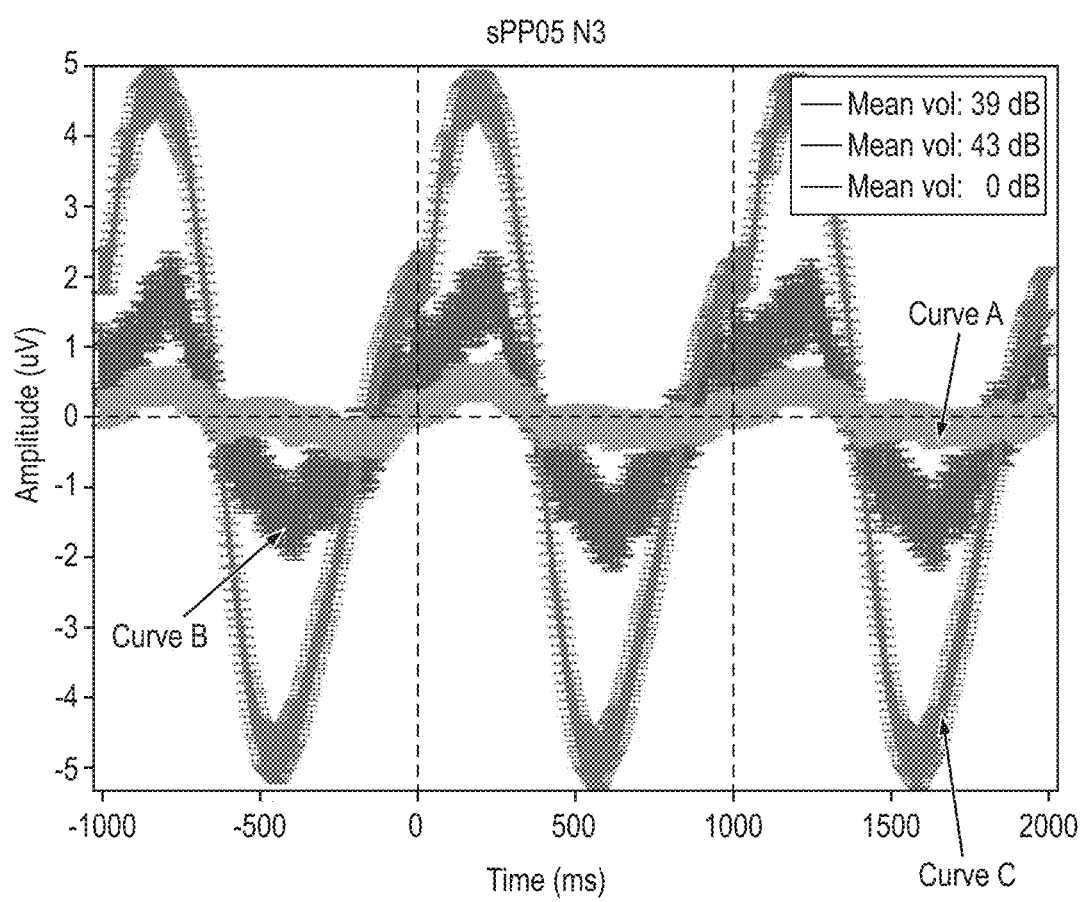
FIG. 1 shows exemplary event related potentials (ERPs) from a single subject under sensory stimulation at different volumes in sleep stage 3 (deep sleep)

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, the term "or" means "and/or" unless the context clearly dictates otherwise.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present patent application provides a system 100 for delivering sensory stimulation. System 100 comprises a sensor 102, a sensory stimulator 104, and a computer system 106. Sensor 102 is configured to measure brain activity information of a patient during a sleep session. Sensory stimulator 104 is configured to deliver sensory stimulation to the patient during the sleep session. The sensory stimulation includes varying stimulation intensity levels. Computer system 106 comprises one or more physical processors 108 operatively connected with sensor 102 and the sensory stimulator 104. One or more physical processors 108 are programmed with computer program instructions which, when executed cause computer system 106 to: determine sleep stage information of the patient based on the brain activity information of the patient during the sleep session; provide input to sensory stimulator 104 based on the determined sleep stage information of the patient, the provided input causing sensory stimulator 104 to deliver the sensory stimulation to the patient; obtain stimulation response information from the patient, the stimulation response information including patient brain response to the delivered sensory stimulation; and determine a range of the stimulation intensity levels within which the patient brain response reaches a threshold. In some embodiments, the fact that it reaches (and exceeds) a threshold indicates that the brain responds to the sensory stimulation.

In some embodiments, patient may be interchangeably referred to as a consumer, a user, an individual or a subject.

An event related potential (ERP) is the measured brain response that is the direct result of a specific sensory, cognitive, or motor event. For example, in some embodiments, it is any stereotyped electrophysiological response to a stimulus. The study of the brain in this way provides a noninvasive means of evaluating brain functioning. In some embodiments, ERPs are measured by means of electroencephalography (EEG). In some embodiments, the magnetoencephalography (MEG) equivalent of ERP is the ERF, or event related field. Evoked potentials and induced potentials are subtypes of ERPs.

In some embodiments, system 100 is configured for identification of an optimal stimulation intensity range for a subject/patient receiving sensory stimulation; and for the estimation of the effect of such sensory stimulation. In some embodiments, system 100 is configured to improve the effectiveness of the existing sleep therapies/devices/systems/portfolios. That is, in some embodiments, system 100 is configured to determine the best stimulation intensity levels (e.g., best volume levels in case of an auditory stimulation) on an individual basis that ensures brain response and that does not disturb sleep. In some embodiments, system 100 provides a consumer tailored solution.

The restorative value of sleep can be increased by enhancing sleep slow waves (SW) using peripheral (e.g., electric, magnetic, or sensory) stimulation during deep sleep. The stimulation is delivered in a closed loop manner to enhance the SWs while avoiding arousals from sleep. The stimulation intensity is one of the factors that determine sensory stimulation effectiveness. Stimulation at low intensity would not enhance slow waves, while stimulation at excessively high intensity could lead to sleep disturbance. System 100 takes into account both: inter- and intra-individual sleep differences. System 100 is based on the fact that increasing stimulation intensity results in an increased amplitude of the corresponding event related brain responses, which is a clear indication of the stimuli salience. In some embodiments, system 100 and method 200 are configured to automatically adjust the intensity range of sensory stimulation during sleep based on evoked response quantification In some embodiments, sensor 102 is configured to measure brain activity information of the patient during the sleep session. In some embodiments, sensor 102 may be referred to as EEG sensing unit. In some embodiments, the EEG sensing unit/sensor 102 is configured to continuously monitor EEG throughout the sleep session of the patient via one or more EEG sensors 102 attached to the patient's head. In some embodiment, signals from the one or more EEG sensors 102 are fed into a signal analysis/processing unit 106.

In some embodiments, information related to brain activity of the patient may include and/or be indicative of slow wave activity (SWA) in the patient (e.g., slow waves, sleep spindles, K-complexes, etc.), sleep pressure in the patient, a sleep stage of the patient, and/or other characteristics of the patient. In some embodiments, sensor 102 may comprise one or more sensors that generate output signals conveying such information directly. For example, sensor 102 may include electrodes configured to detect electrical activity resulting from current flows within the brain of the patient.

In some embodiments, sensor 102 may comprise one or more sensors that generate output signals conveying information related to brain activity during sleep of the patient indirectly. For example, one or more sensors 102 may generate an output based on a heart rate of the patient (e.g., sensor 102 may be a heart rate sensor), movement of the patient (e.g., sensor 102 may include an accelerometer such that sleep may be analyzed using actigraphy signals), ocular activity, facial muscle activity, respiration of the patient, and/or other characteristics of the patient. In some embodiments, a portion of sensor 102 is formed by the conductive material described above that contacts the ear of the patient.

As another example, the information related to the brain activity of the patient may be obtained from one or more monitoring devices (e.g., EEG monitoring device, or other brain activity monitoring devices). In some embodiments, one or more monitoring devices and associated sensors 102 may be configured to monitor the brain activity of patient. These monitoring devices may include one or more sensors 102. Sensor 102 may, for instance, be configured to obtain information related to the brain activity of patient.

Figure 3:
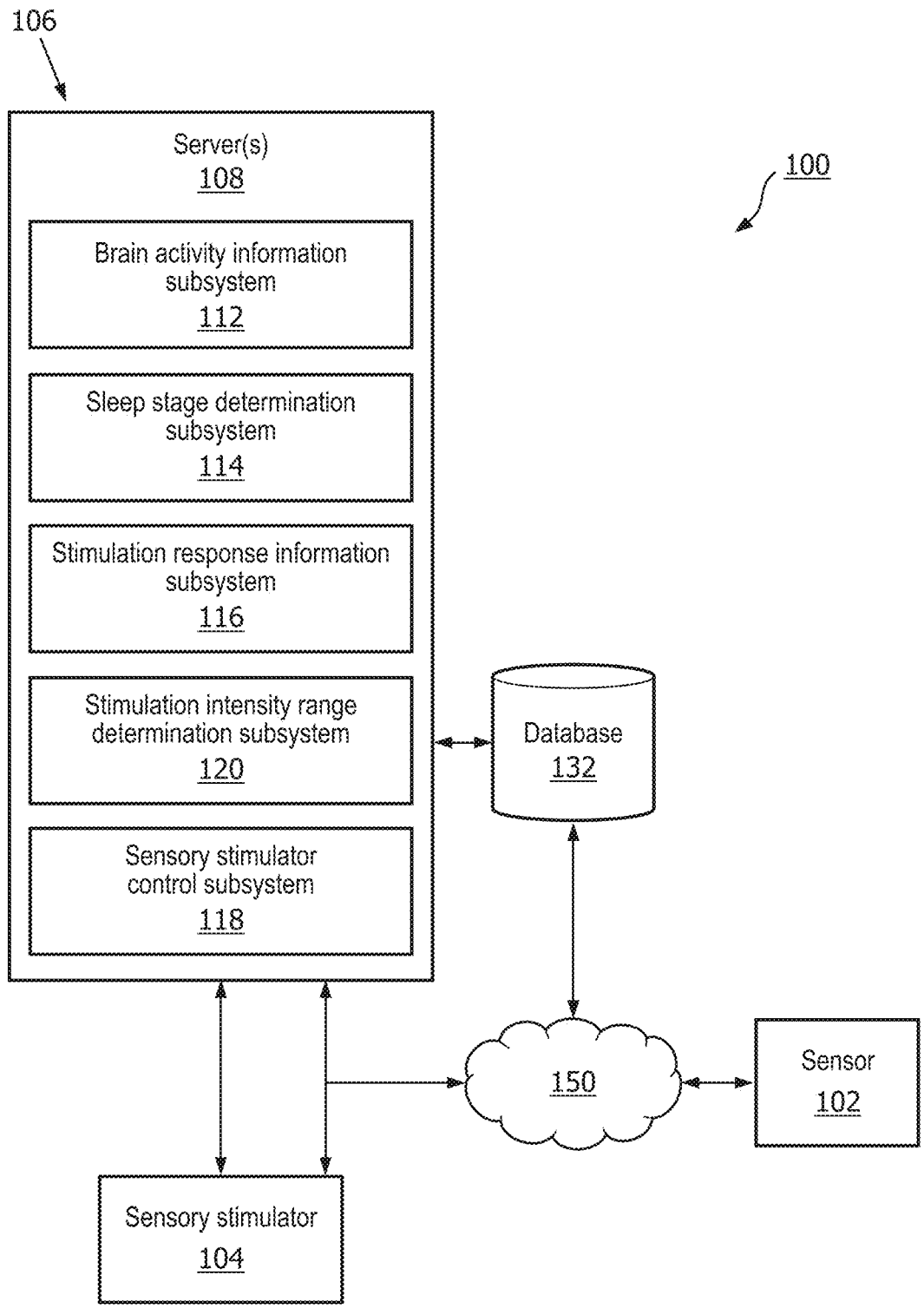
FIG. 3 shows another exemplary system for delivering sensory simulation in accordance with an embodiment of the present patent application.

In some embodiments, sensor 102 includes a transmitter for sending signals/information and a receiver for receiving the signals/information. In some embodiments, sensor 102 is configured to communicate wirelessly with computer system 106. As shown in FIG. 3, in some embodiments, sensor 102 is configured to be operatively connected with computer system 106 and/or one or more physical processors 108 of computer system 106. In some embodiments, sensor 102 is configured to communicate with sensory stimulator 104. In some embodiments, sensor 102 is in communication with a database 132. In some embodiments, the information related to the brain activity of the patient may be obtained from the database 132 that is being updated in real-time by sensor 102.

In one scenario, a monitoring device may obtain information (e.g., based on information from sensor 102), and provide information to computer system 106 (e.g., comprising server 108) over a network (e.g., network 150) for processing. In another scenario, upon obtaining the information, the monitoring device may process the obtained information, and provide processed information to computer system 106 over a network (e.g., network 150). In yet another scenario, the monitoring device may automatically provide information (e.g., obtained or processed) to computer system 106 (e.g., comprising server 108).

In some embodiments, sensor 102 is configured to generate output signals conveying information related to brain activity of the patient and/or other information. Sensor 102 is configured to generate output signals in an ongoing manner during the sleep session of the patient, at regular intervals during the sleep session, and/or at other times. In some embodiments, the brain activity of the patient may correspond to a current sleep stage, SWA in the patient, and/or other characteristics of the patient. In some embodiments, the brain activity of the patient may be associated with rapid eye movement (REM) sleep, non-rapid eye movement (NREM) sleep, and/or other sleep. In some embodiments, sleep stages of the patient may include one or more of NREM stage N1, stage N2, or stage N3 sleep, REM sleep, and/or other sleep stages. In some embodiments, N1 corresponds to a light sleep state and N3 corresponds to a deep sleep state. In some embodiments, NREM stage 3 or stage 2 sleep may be slow wave (e.g., deep) sleep. In some embodiments, sensor 102 may comprise one or more sensors that measure such parameters directly and/or indirectly. For example, sensor 102 may include electrodes configured to detect electrical activity along the scalp of the patient resulting from current flows within the brain of the patient. In some embodiments, one or more sensors 102 are EEG electrodes, and/or other sensors. In some embodiments, an EEG exhibits changes throughout a sleep session of the patient. In some embodiments, a prominent change in the EEG delta power (also known as slow wave activity (SWA)) is typically visible, for example.

Although, in some embodiments, sensor 102 may be positioned at a single location near the patient, this is not intended to be limiting. Sensor 102 may include one or more sensors disposed in a plurality of locations, such as for example, coupled in a removable manner with the skin of the patient, coupled in a removable manner with clothing of the patient, worn by the patient (e.g., as a headband, a wristband, a hood worn by the patient etc.), and/or in other locations. For example, sensor 102 may be removably coupled with the skin of the patient via a sticker and/or other coupling mechanisms. In some embodiments, sensor 102 is placed slightly below the mastoid of the patient near major arteries of the patient. In some embodiments, sensor 102 are attached to the patient with stickers. In some embodiments, sensor 102 is either applied to directly to a patient's head or integrated into some kind of cap to be worn by the patient.

In some embodiments, sensory stimulator 104 is also referred to as an actuator or a stimulation actuator. In some embodiments, sensory stimulator 104 is configured to receive information from computer system 106 and to generate and provide sensory stimulation to the patient based on the received information. In some embodiments, sensory stimulator 104 is configured to stop, continue/resume, adjust, or start sensory stimulation provided to the patient based on the information received from computer system 106.

In some embodiments, the received information from computer system 106 may include determined sleep stage information. In some embodiments, the determined sleep stage information, among other things, includes simulation timing when the sensory stimulation is delivered to the patient. In some embodiments, sensory stimulator 104 is configured to generate and provide sensory stimulation based on the determined sleep stage information. In some embodiments, sensory stimulator 104 is configured to adjust the stimulation intensity of sensory stimulation provided to the patient based on the information received from computer system 106.

In some embodiments, the sensory stimulation provided by sensory stimulator 104 has varying stimulation intensity levels.

In some embodiments, sensory stimulator 104 is configured to provide sensory stimulation to the patient during the least arousable state of the patient based on the received information related to the brain activity of the patient.

In some embodiments, sensory stimulator 104 is configured to provide sensory stimulation to the patient prior to a sleep session, during a sleep session, after a sleep session, and/or at other times. In some embodiments, sensory stimulator 104 is configured to provide sensory stimulation to the patient without causing arousals during sleep. In some embodiments, for example, sensory stimulator 104 may be configured to provide sensory stimulation to the patient during slow wave sleep in the sleep session. In some embodiments, sensory stimulator 104 may be configured to provide sensory stimulation to the patient to induce and/or adjust slow wave activity (SWA) in the patient. In some embodiments, sleep slow waves are associated with slow wave activity (SWA) in the patient during the sleep session.

In some embodiments, sensory stimulator 104 is configured such that inducing and/or adjusting SWA includes inducing, increasing, and/or enhancing sleep slow waves in the patient.

In some embodiments, sensory stimulator 104 may be configured to induce, increase, and/or enhance sleep slow waves through non-invasive brain stimulation and/or other methods. In some embodiments, sensory stimulator 104 may be configured to induce, increase, and/or enhance sleep slow waves through non-invasive brain stimulation using sensory stimulation.

In some embodiments, system 100 is configured to be applied for various types of sensory stimulation, including auditory, visual and somatosensory stimuli. In some embodiments, the sensory stimulation may include different types of sensory stimulations. In some embodiments, the sensory stimulation is selected from the group consisting of olfactory stimulation, somatosensory stimulation, auditory stimulation, visual stimulation, touch stimulation, taste stimulation, and haptic stimulation. In some embodiments, the sensory stimulation may include smells, tones, odors, sounds, visual stimulation (e.g., lights flashed on open and/or closed eyes), touches, tastes, haptic (e.g., vibrations or non-contact haptic) stimulation, and/or other sensory stimulations. In some embodiments, for example, acoustic tones may be provided to the patient to induce, increase, and/or enhance sleep slow waves. In some embodiments, examples of sensory stimulator 104 may include one or more of a music player, a tone generator, a collection of electrodes on the scalp of the patient, a unit to deliver vibratory stimulation (also known as somato-sensory stimulation), a coil generating a magnetic field to directly stimulate the brain's cortex, light generators, a fragrance dispenser, and/or other sensory stimulators.

In some embodiments, sensory stimulator 104 includes wireless audio device and one or more audio speakers. In some embodiments, a headband may be worn by the patient. In some embodiments, the headband includes the wireless audio device and the one or more audio speakers. In some embodiments, the one or more audio speakers may be located in and/or near the ears of the patient.

In some embodiments, interchangeable earbud attachments in a range of sizes (e.g., small (S), medium (M), and large (L) are configured to removably couple with a housing of ear insert such that the patient may find an interchangeable earbud attachment that is most comfortable and attach it to the housing. In some embodiments, earbud attachments are formed from the conductive materials such that earbud attachments form a portion of sensor 102.

In some embodiments, the housing includes electronic components that form a portion of sensor 102, sensory stimulator 104, and/or other components of system 100. In some embodiments, sensory stimulator 104, sensor 102 are formed integrally with the ear insert such that the ear insert, sensory stimulators 104, and sensor 102 appear to form a single unified physical object that is comfortable for the patient to insert and remove from his or her ears. In some embodiments, the ear insert is custom formed based on three dimensional data representative of the ear of the patient, a physical mold/model of the ear of the patient, and/or other information. Whether a custom ear insert is fabricated directly based on the three dimensional data or fabricated from a mold or other components formed based on the three dimensional data, the ear insert may be customized based on the three dimensional data to fill the ear canal of the patient and much of the outer ear of the patient without protruding from the head of the patient so as to enable comfort during sleep and/or other activities (e.g., maximizing the surface area ear insert that is in contact with the ear of the patient without hindering comfort). In some embodiments, the ear insert may be customized to include a small canal built into the ear insert (e.g., with an approximate diameter of about 2-3 mm) to facilitate hearing ambient sounds (e.g., during sleep and/or while awake). In some embodiments, the ear insert may be customized such than an area of the ear insert under the tragus of the patient is smoothed to allow the tragus room for lying against the earpiece should the patient elect to sleep on their side, for example.

In some embodiments, the housing and the earbud attachments form correspond clamping or other engagement surfaces configured to removably couple with each other. In some embodiments, engagement surface on the housing includes a conductive surface such that electrical signals passing through the earbud attachments are received by the housing. In some embodiments, the housing may include one or more features (e.g., a hook that wraps around the ear of the patient) to enhance coupling with the ear of the patient. In some embodiments, the ear insert are made at three different levels of material elasticity (e.g., very soft, soft, and hard).

In some embodiments, system 100 includes computer system 106 that comprises one or more physical processors 108 operatively connected with sensor 102 and sensory stimulator 104. In some embodiments, one or more physical processors 108 are programmed with computer program instructions which, when executed cause computer system 106 to perform various functions.

As shown in FIG. 3, system 100 may comprise server 108 (or multiple servers 108). In some embodiments, server 108 includes one or more physical/hardware processors 108. In FIG. 3, database 132 is shown as a separate entity, but, in some embodiments, database 132 could be part of computer system 106. As will be clear from the discussions above and below, in some embodiments, system 100 includes computer system 106 that has one or more physical/hardware processors 108 programmed with computer program/machine readable instructions that, when executed cause computer system 106 to obtain information/data from sensor 102. In some embodiments, computer system 106 may also be referred to as means 106 for executing machine readable instructions with at least one hardware processor 108.

In some embodiments, server 108 comprises brain activity information subsystem 112, sleep stage determination subsystem 114, stimulation response information subsystem 116, stimulation intensity range determination subsystem 120, sensory stimulator control subsystem 118 or other components or subsystems. In some embodiments, brain activity information subsystem 112, sleep stage determination subsystem 114, stimulation response information subsystem 116, stimulation intensity range determination subsystem 120, sensory stimulator control subsystem 118 or other components or subsystems together may be referred to as signal processing or signal analysis device/unit.

In some embodiments, brain activity information subsystem 112 is configured to receive or obtain the brain activity information of the patient from sensor 102. In some embodiments, brain activity information subsystem 112 is configured to further process the received or obtained brain activity information. In some embodiments, brain activity information subsystem 112 comprises a brain activity signal feature extraction unit that is configured to extract the brain activity features from the signals, data or information provided by sensor 102. In some embodiments, brain activity information subsystem 112 is optional and the brain activity information of the patient from sensor 102 may be directly received or obtained by sleep stage determination subsystem 114. In such an embodiment, sleep stage determination subsystem 114 comprises a brain activity feature extraction unit that is configured to extract the brain activity features from the signals, data or information provided by sensor 102.

In some embodiments, sleep stage determination subsystem 114 is configured to extract a characteristic from the signals or information obtained from sensor 102 and that is proportional to the brain activity. In some embodiments, sleep stage determination subsystem 114 includes extraction algorithms configured to extract a characteristic from the signals or information obtained from sensor 102 and that is proportional to the brain activity. In some embodiments, sleep stage determination subsystem 114 includes machine learning based methods (i.e., that were trained using historical data/information) are configured to extract a characteristic from the signals or information obtained from sensor 102 and that is proportional to the brain activity. In some embodiments, sleep stage determination subsystem 114 includes a processing module or a signal processing module.

In some embodiments, sleep stage determination subsystem 114 is configured to determine sleep stage information of the patient based on the brain activity information (from sensor 102) of the patient during the sleep session. In some embodiments, sleep stage information includes 1) sleep stage the user/patient is currently in; 2) sleep depth; 3) information about arousals; and 4) stimulation timing information (i.e., time when sensory stimulation can be delivered to the patient).

Signal analysis unit is not limited to the blocks described above. In some embodiments, sleep stager/sleep stage determination subsystem 114 may be replaced by any logic that estimates (optimal) stimulation timing or omitted. In some embodiments, sleep stage determination subsystem 114 is configured to use state of the art sleep staging algorithms to automatically detect the sleep stage the subject is currently in. Additionally, in some embodiments, sleep stage determination subsystem 114 is configured to monitor sleep depth and arousals. Based on this information, sleep stage determination subsystem 114 is configured to define the stimulation time when sensory stimulation can be delivered to the patient. In some embodiments, this information (i.e., the time when sensory stimulation can be delivered to the patient) is sent to sensory stimulator control subsystem 118.

In some embodiments, sensory stimulator control subsystem 118 is configured to receive information (from sleep stage determination subsystem 114) and to provide input to sensory stimulator 104 based on the received information, the provided input causing sensory stimulator 104 to deliver the sensory stimulation to the patient based on the determined sleep stage information. In some embodiments, the provided input includes starting, continuing/resuming, adjusting or stopping the sensory stimulation. In some embodiments, computer system 106 is configured to adjust, in real-time or near real-time, the stimulation intensity (e.g., volume) of the sensory stimulation to enhance the sleep slow waves without provoking arousals in the patient.

An arousal event may include waking from sleep and/or other arousal events associated with wakefulness of the patient. Responsive to detecting the possible arousal event, sensory stimulator control subsystem 118 may cause sensory stimulator 104 to cease providing sensory stimulation and then determine whether the possible arousal event was a false arousal event. In some embodiments, responsive to determining that the possible arousal event was a false arousal event, sensory stimulator control subsystem 118 may cause sensory stimulator 104 to resume/continue providing sensory stimulation with an intensity determined based on the recently determined sleep stage information and the recent brain activity information.

In some embodiments, stimulation response information subsystem 116/stimulation response unit is configured to monitor the immediate response to the sensory stimulation delivered to the patient.

In some embodiments, the stimulation response information includes patient brain response to the delivered sensory stimulation. In some embodiments, the stimulation response information is measured by the same sensor, sensor 102. In some embodiments, the stimulation response information includes a waveform, an amplitude of positive and/or negative peaks in the waveform, peak to peak distance in the waveform, an average amplitude of the waveform, latency of the successive peaks in the waveform, and an area under the waveform in a predefined intervals. In some embodiments, stimulation response information is in the form of a waveform. In some embodiments, stimulation response information includes 1) amplitude of the waveform, 2) latency of the successive peaks, 3) area under the curve are extracted from the waveform, and other stimulation response information that can be extracted from such a waveform.

In some embodiments, stimulation response information subsystem 116/stimulation response unit is also configured identify the minimum and/or the maximum stimulation intensity level.

In some embodiments, stimulation intensity range determination subsystem 120 is configured to identify the minimum and/or the maximum stimulation intensity levels. In some embodiments, stimulation intensity range determination subsystem 120 is configured to determine a stimulation intensity range for the patient based on the obtained stimulation response information from stimulation response information subsystem 116/stimulation response unit. In some embodiments, stimulation intensity range includes a minimum stimulation intensity level and a maximum stimulation intensity level.

In some embodiments, stimulation response information subsystem 116/stimulation response unit or stimulation intensity range determination subsystem 120 is configured to determine a stimulation intensity range for the patient based on the obtained stimulation response information. In some embodiments, the range of the stimulation intensity levels includes a minimum stimulation intensity level and a maximum stimulation intensity level. In some embodiments, the minimum stimulation intensity level is the lowest stimulation intensity level for which the delivered sensory stimulation elicits a detectable patient brain response. In some embodiments, the maximum stimulation intensity level the highest stimulation intensity level for which the patient brain response has reached a saturation level. In some embodiments, the range of the stimulation intensity levels also includes a baseline stimulation intensity level. In some embodiments, the minimum stimulation intensity level is the lowest stimulation intensity level for which the obtained stimulation response information reaches a difference from the baseline stimulation intensity level, and the maximum stimulation intensity level is the highest stimulation intensity level for which the obtained stimulation response information reaches a difference from the baseline stimulation intensity level.

In some embodiments, maximum stimulation intensity level is the stimulation intensity level at which the patient brain response does not change any further (i.e., patient brain response has reached saturation). In some embodiments, maximum stimulation intensity level is below the stimulation intensity that produces arousals.

In some embodiments, minimum stimulation intensity level is the lowest stimulation intensity level at which desired features are above the pre-defined threshold. In some embodiments, minimum stimulation intensity level is the stimulation intensity level at which there is a detectable patient brain response.

In some embodiments, stimulation intensity range also includes a baseline stimulation intensity. In some embodiments, the baseline stimulation intensity is the stimulation intensity at which there is no patient brain response.

Optionally, system 100 is configured to communicate to the user interface 160 of system 100 if the sensory stimulation triggered any patient brain response.

In some embodiments, stimulation response unit/stimulation response information subsystem 116 or stimulation intensity range determination subsystem 120 is configured to calculate an event related response (ERP) around sensory stimulation onset over a number of stimulation events (including the case of a single simulation event).

In some embodiments, the event related response is calculated as the time-locked average of the raw signal (i.e., event related response, ERP) or the EEG power in a given frequency band (i.e., desynchronization (ERD) or synchronization (ERS)) in a window of fixed duration aligned around stimulation onset. Then, amplitude and latency of the successive peaks in the resulting stimulation response waveform, the area under the curve and other relevant features, depending of stimulation modality, are extracted.

Figure 4A:
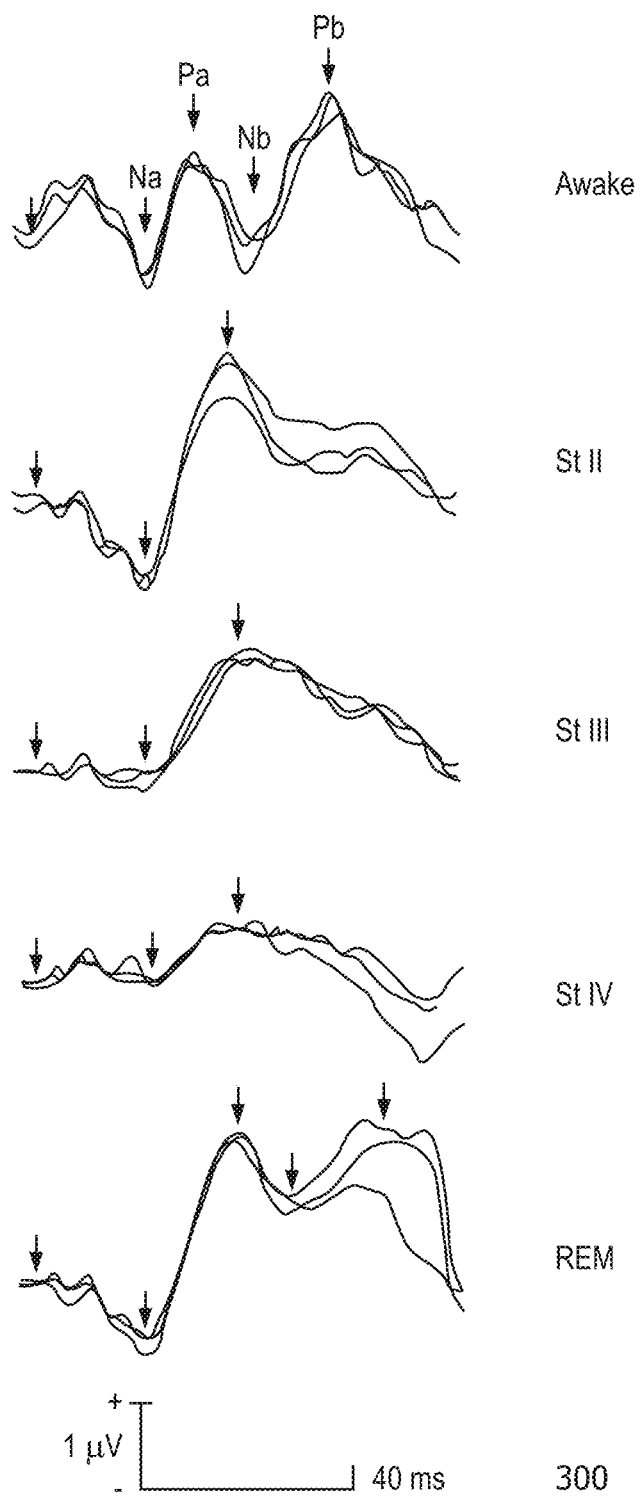
FIGS. 4A-4C show exemplary stereotypical event-related brain responses.
Figure 4B:
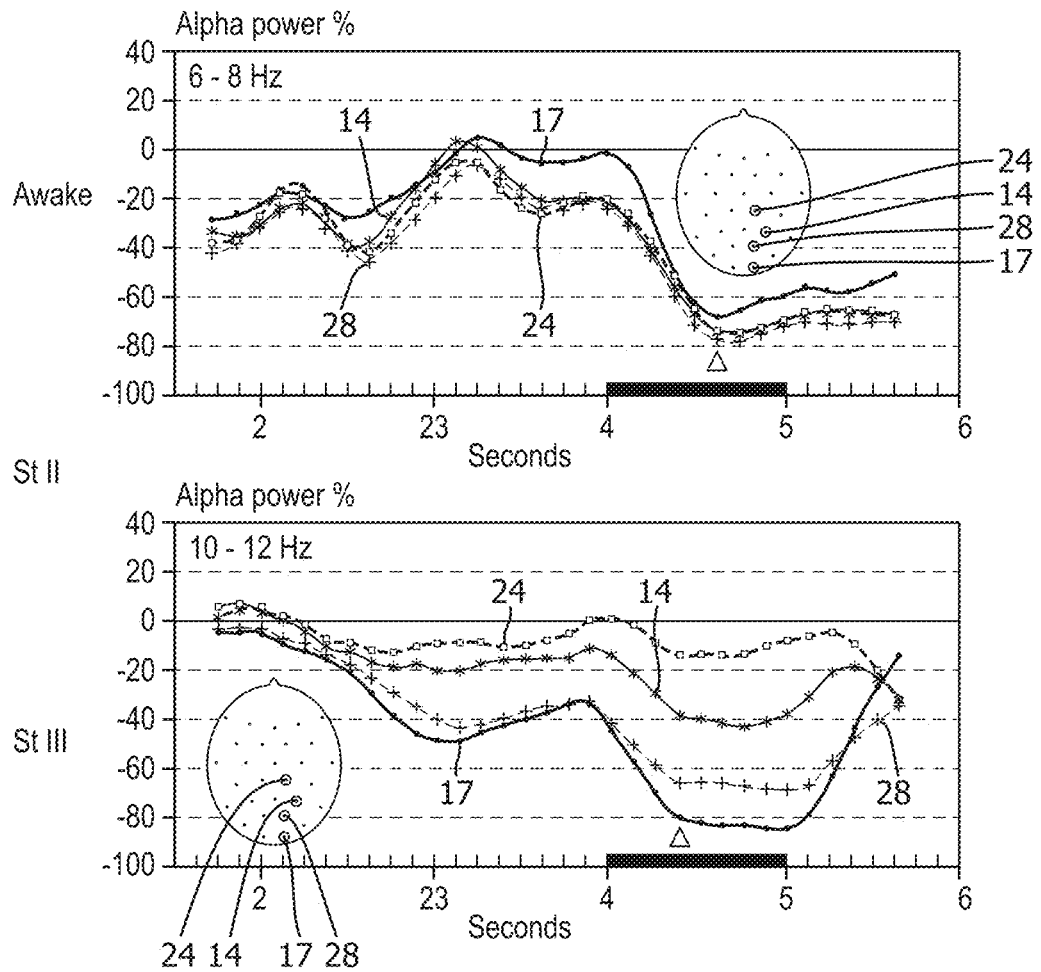
Figure 4C:
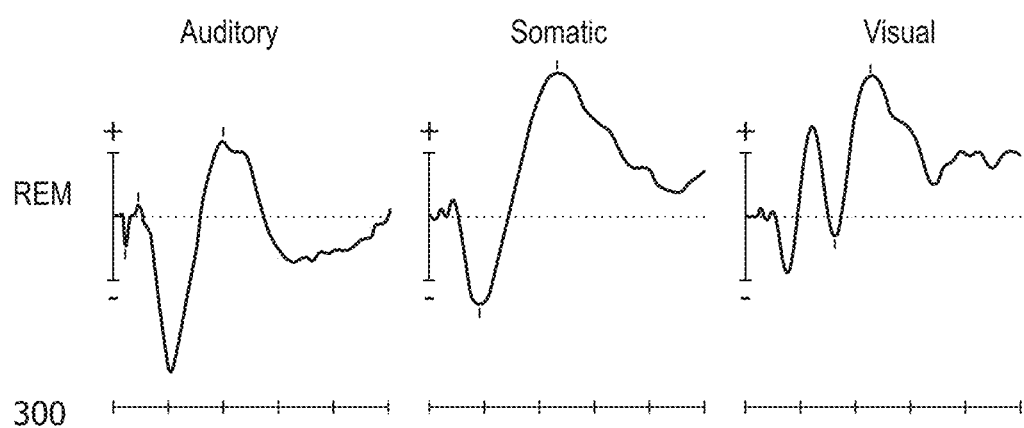

Some examples of stereotypical responses to stimuli of different modalities and in different states of wakefulness and sleep are shown in FIGS. 4A-4C. FIGS. 4A-4C show exemplary stereotypical event-related patient brain responses. For example, FIG. 4A shows auditory evoked potentials (AEP) traces during wakefulness and different sleep stages recorded at Fz; FIG. 4B shows event-related desynchronization (ERD) time courses calculated during 1-$s$ red light stimulation (black bar); and FIG. 4C shows sensory evoked potentials in different modalities during wakefulness. St II to St IV in FIG. 4A stand for sleep stages S2 to S4, respectively.

In some embodiments, stimulation response unit/stimulation response information subsystem 116 or stimulation intensity range determination subsystem 120 is configured to determine a range of the stimulation intensity levels within which the patient brain response reaches a threshold. In some embodiments, the threshold is predetermined or pre-defined.

In some embodiments, stimulation response unit/stimulation response information subsystem 116 or stimulation intensity range determination subsystem 120 is configured to calculate minimum stimulation intensity level of the range of the stimulation intensity levels within which the patient brain response reaches the threshold. In some embodiments, the minimum stimulation intensity level is the lowest intensity for which a stimulus elicits a detectable patient brain response. In some embodiments, to calculate the lower stimulation boundary, for different stimulation intensities or intensity intervals, including zero, a number of stimuli (trials) are presented to the sleeping subject/patient (controlling for sleep depth). In some embodiments, for a reliable estimation, a sufficient number of stimuli needs to be applied (at least 100 per stimulation intensity).

In some embodiments, the stimuli/sensory stimulation of different intensities can be delivered in a sequential or randomized order or using the staircase procedure from psychophysics. In all cases, for each considered stimulation intensity, the average EEG response in a window of pre-defined duration around stimulation onset is calculated over all trials at that intensity. Then, relevant features are extracted. In some embodiments, the features include the amplitude of first/second/etc. positive or negative peaks in the stimulation response waveform; peak to peak distance; and/or average amplitude or area under the curve in a predefined intervals and others.

In some embodiments, to enhance signal to noise ratio, various filtering or fitting procedures could be applied before extracting the features. In some embodiments, additionally, single trial waveforms containing extreme values can be identified as containing artifacts and excluded prior to calculating the averaged response using absolute or relative thresholds (e.g., amplitude above 200 µV, or amplitude exceeding the mean EEG amplitude by, e.g., two standard deviations).

Figure 5:
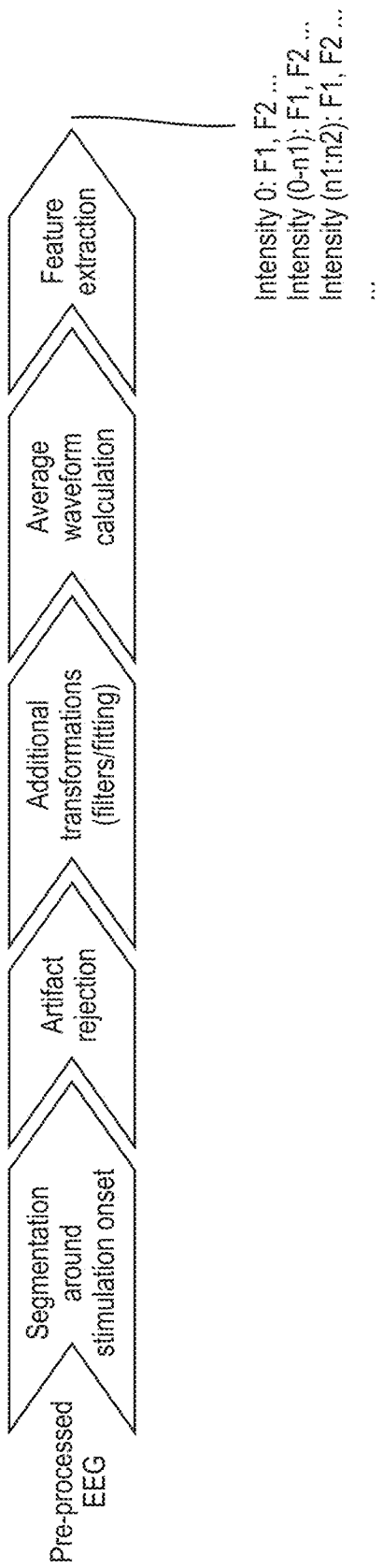
FIG. 5 shows exemplary processing procedures/steps for determining minimum stimulation intensity level in accordance with an embodiment of the present patent application.

In some embodiments, the processing steps for determining the range of the stimulation intensity levels within which the patient brain response reaches the threshold are visualized in FIG. 5. In FIG. 5, processing steps. n1, n2, . . . refer to intensity limits; F1, F2, . . . are the extracted features.

Referring to FIG. 5, in some embodiments, system 100 is configured to pre-process the brain activity information (e.g., from sensor 102) of the patient during the sleep session; perform segmentation around the sensory stimulation onset; reject artifacts (optional procedure); perform additional transformation including filters and fitting (optional procedure); to calculate average stimulation response waveform; and to extract the features.

In some embodiments, the features for each stimulation intensity group (i.e., the tested values), which are technically the group mean, are then statistically compared to a baseline. This can be one of the following: 1) the features calculated for the stimulation intensity group of intensity 0 from the same night, 2) the features calculated for all trials during a sham (no stimulation) night, 3) a mean over a sample of the same size of random EEG excerpts, and 4) a constant.

In some embodiments, there are several statistical tests that allow testing the difference between the mean values of two or more groups. Each statistical test has particular requirements that need to be met in order to be applied to the data. For example, for a t-test or ANOVA: the tested variables must be continuous (interval/ratio) and approximately normally distributed, the samples must be independent of one another and they do not contain outliers. Non-parametric tests, such as Wilcoxson signed rank test, make no assumptions about the probability distributions of the tested variables but require the data to be paired and to come from the same population and each pair must be chosen randomly and independently. Assuming that necessary requirements are met, the two probability distributions (of the tested variable and the baseline variable) are compared and a probability of rejecting a hypothesis that there is no difference between the 2 means when that is the case (the null hypothesis) is calculated. This probability, called p-value, is compared to a pre-chosen probability, called significance level (usually $\alpha=0.05$). If the calculated p-value is smaller than the chosen significance level, then the null hypothesis is rejected and it can be said that there is a difference between the tested value and the baseline. To counteract the increased chance of rejecting the null hypothesis when multiple tests are carried out, the value of a can be reduced proportionally to the number of test carried out via a procedure known in statistics as Bonferroni correction.

Such correction is, however, simply equivalent to selecting another (stricter) significance level. In some embodiments, the minimum stimulation intensity level is then defined as the lowest stimulation intensity level for which any of the extracted features shows a significant difference from the baseline.

Figure 6:
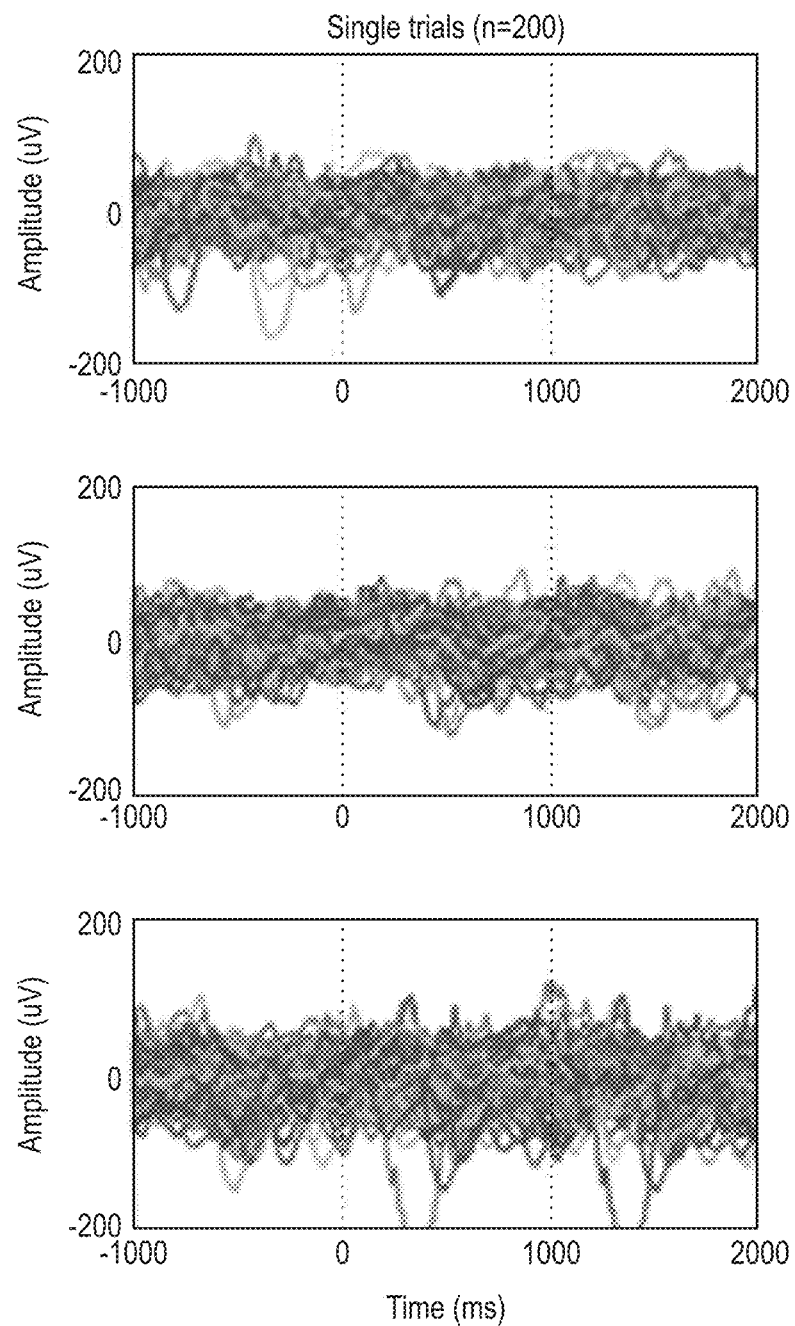
FIG. 6 shows exemplary features extracted from an auditory evoked ERP during sleep stage 3 in three different volume groups in accordance with an embodiment of the present patent application.
Figure 6:
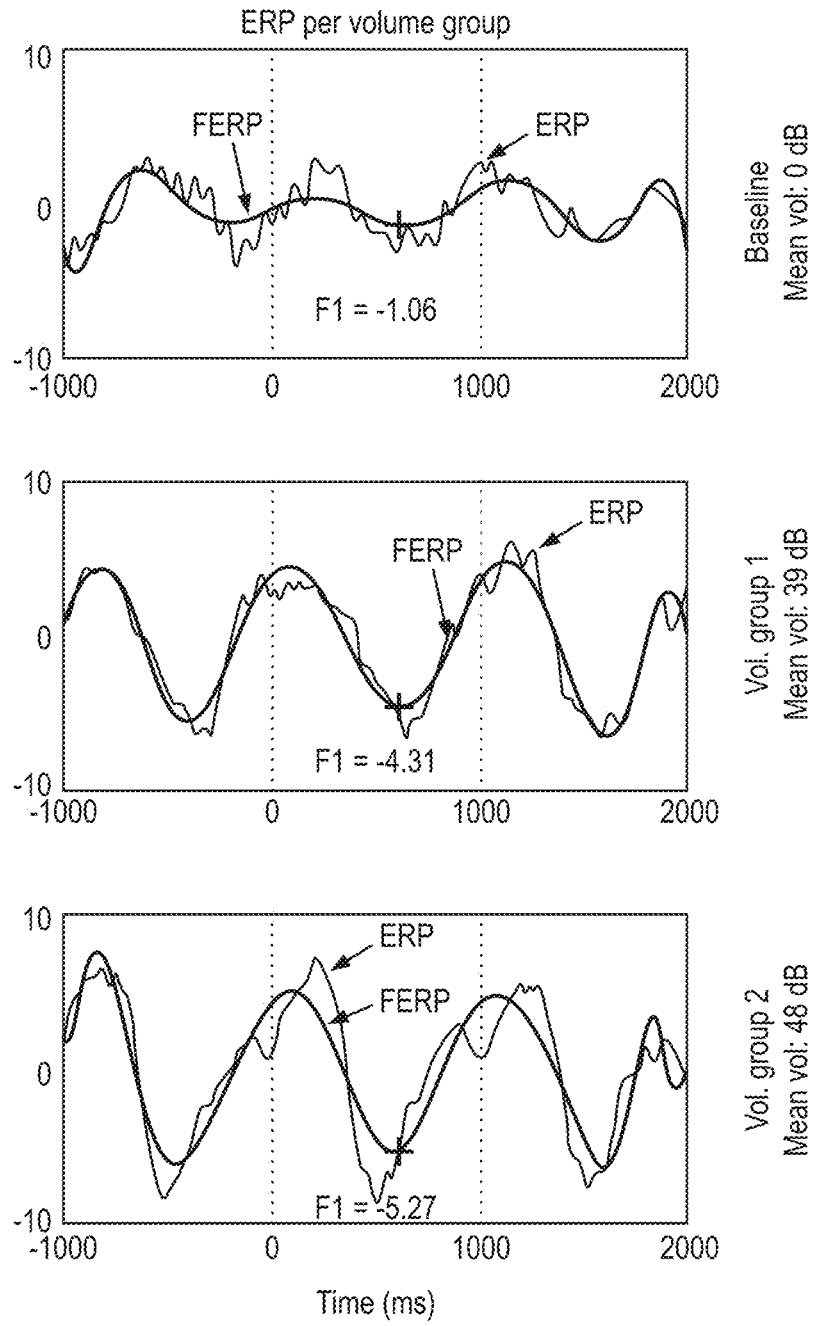

FIG. 6 shows a concrete example of the concept described so far in the context of auditory stimulation. Tones of different volumes (n=200 per volume group) are delivered during a sleep session in sleep stage 3 (or sleep stage 2). Three-second long segments around tone onset (i.e., starting a second before and ending 2 seconds after stimulus onset) are extracted from the pre-processed EEG signal (or the brain activity information). For each volume group, the time locked average (the ERP) is calculated and, optionally, a polynomial of order 10 is fitted. Then, the first negative peak after 250 milliseconds (ms) from tone onset (i.e., feature F1) is detected. The value of F1 is the mean EEG amplitude at that point. So, if the difference between the mean EEG amplitude of each volume group and the baseline (vol=0 dB) is to be tested, the distributions of amplitudes at the time where feature F1 is calculated for each trial in both groups (see FIG. 7) are compared. The amplitude values are normally distributed, and a t-test is applied to determine if the means of the two groups are statistically different. The test between Vol group 1 (with mean volume of 39 dB) and the baseline (mean volume 0 dB) results in a p-value=0.0371, which is smaller than $\alpha$=0.05, hence the two means are statistically significantly different. The test between Vol group 2 (mean volume 48 dB) and the baseline gives a p-value=0.0026, which is also significant.

Hence, Vol group 1 (with mean volume of 39 dB) is selected as the minimum volume for that subject. Alternative features applicable to this example include the amplitude of the first positive peak in the first 250 milliseconds (ms), the mean amplitude in a window of 100 milliseconds (ms) surrounding the positive or the negative peaks, and the absolute peak to peak difference.

FIG. 6 shows exemplary features extracted from an auditory evoked ERP during sleep stage 3 in three different volume groups (in the rows). The graphs of the original portion of FIG. 6 show amplitude (measured in microvolts) on the Y-axis. Time is on the X-axis of the graph and is measured in milliseconds. The graphs in the continuation portion of FIG. 6 show the amplitude of the average of signals displayed on the the original portion of the FIG. 6 graphs (measured in microvolts) on the Y-axis. Time is on the X-axis of the graph and is measured in milliseconds. The top most set of the graphs in FIG. 6 and the continuation portion of FIG. 6 show data for mean volume of 0 dB. The middle set of the graphs in FIG. 6 and the continuation portion of FIG. 6 show data for mean volume of 39 dB. The bottom most set of the graphs in FIG. 6 and the continuation portion of FIG. 6 show data for mean volume of 48 dB.

The graphs in FIG. 6 show three-second long groups of EEG traces around the tones. In FIG. 6, left hand side graphs show stimuli onset (e.g., at 0 and 1000, shown by dotted lines), traces ERP in the plots in column 2/right side graphs are the ERPs calculated using the trials shown in the plots from column 1/left side graphs, and traces FERP indicate the 10th order polynomial fit of the ERP. The black "+" sign indicates the selected feature F1 coinciding with the first negative peak 250 millimeters (ms) after stimulus onset.

Figure 7:
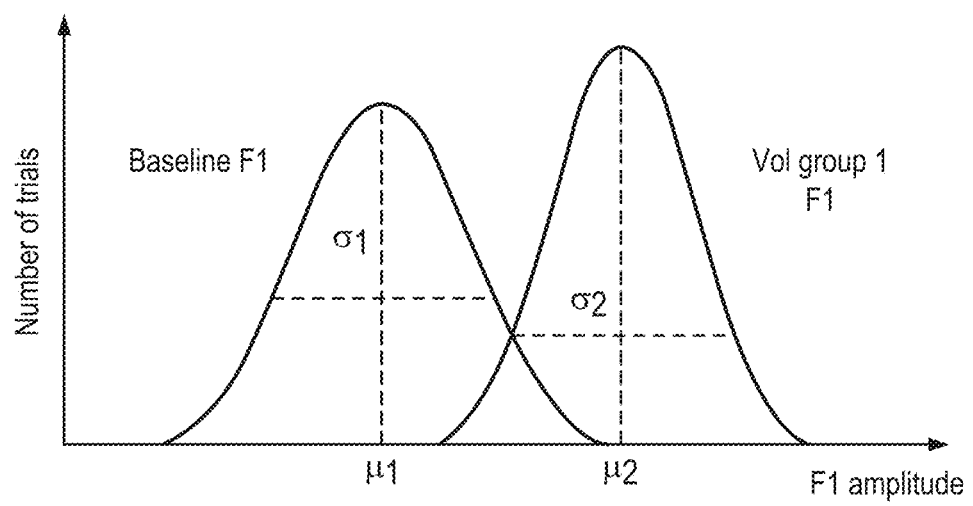
FIG. 7 shows exemplary feature distributions in accordance with an embodiment of the present patent application.

FIG. 7 shows an exemplary feature distributions in accordance with the embodiments of the present patent application. The graph of FIG. 7 shows number of trials on the Y-axis. Amplitude is on the X-axis of the graph of FIG. 7 and is measured in microvolts.

In some embodiments, a simple thresholding can be applied. Then, the minimum stimulation intensity level is defined as the lowest stimulation intensity for which any of the features crosses a pre-defined or a predetermined threshold. If the example above is used and a threshold of −4, the minimum volume would be the lowest volume at which feature F1 is lower than −4. The threshold can also be set as a proportion of the baseline level (e.g., 3 times bigger than baseline, or baseline mean plus twice the standard deviation).

In some embodiments, if the staircase procedure is used, the stimulation intensity level is changed on a trial by trial basis according to the detected patient brain response. Starting from one side of the scale, say a high stimulation intensity level, trials of that stimulation intensity are delivered. If patient brain response is detected (by any of the ways described above), the stimulation intensity is reduced until no response is detected. Then, the stimulation intensity is again increased step-wise until a patient brain response is detected, at which point the intensity is lowered again. The procedure continues for a predefined number of transition points, or reversals. The minimum stimulation intensity level is then identified as the point at which the staircase converges or as the mean of the last few (e.g., 3) reversal points. In order to account for EEG variability, multiple trials at the same stimulation intensity could be used at each staircase step.

In some embodiments, determining the minimum stimulation intensity level in practice could be a strategy applied if a predefined stimulation intensity, which was shown to be effective, causes arousals. In this case, this "default" stimulation intensity is too high for the particular user and a new effective minimum stimulation intensity level needs to be found using the strategy described above.

The maximum stimulation intensity level is the maximum value at which stimuli are presented to the user during a sleep session. The maximum stimulation intensity level does not have to exceed levels that might be harmful for the user, thus, the maximum stimulation intensity level should always fall under the accepted safety standards (for example for auditory stimulation, volume levels louder than 85 dB are considered as potentially harmful). In some embodiments, additionally, the maximum stimulation intensity level has to be higher than the minimum stimulation level that has been set using the procedure described in the previous section.

In some embodiments, to choose the maximum stimulation intensity level, the feature extraction procedure outlined above can be used. For each stimulation intensity group that 1) has reached statistical significance, and 2) is below the safety standard levels, the feature's percentage increase from baseline can be calculated. Then, the maximum stimulation level can be selected as the lowest intensity value for which this percentage exceeds a predefined/predetermined threshold. In the example with auditory evoked ERPs, the maximum volume could be set at the volume group for which feature F1 is, say, at least 5 times bigger than baseline.

In some embodiments, similar to the minimum stimulation intensity selection, simple thresholding can also be applied. Then, the maximum stimulation intensity level is defined as the lowest intensity for which any of the features crosses a pre-defined/predetermined threshold. If the example above was used and a threshold of −5, the maximum volume would be the lowest volume at which feature F1 is lower than −5.

The selected maximum intensity can also be determined as the intensity prior to reaching a saturation of the effect. In other words, when increasing the intensity does not show any or at least not a significant increase in the features evaluated.

In some embodiments, stimulation intensity level does not have to cause arousals from sleep, hence the maximum stimulation intensity level can be also selected as the highest intensity at which no arousal has been reached. In some embodiments, the features used would be binary values indicating whether a micro-arousal has been provoked or not. Then, the maximum stimulation intensity level would be the lowest stimulation intensity level for which significant difference in the percentage arousing trials between that group and baseline is detected using any statistical test assuming binomial distribution of the tested variables.

In some embodiments, patient brain oscillations in the alpha (8-12 Hz) and beta (12-30 Hz) EEG bands have been associated with arousals. Hence, the ERD/ERS response in those bands can also be used to set the maximum stimulation intensity level. In some embodiments, an alpha and/or beta ERS exceeding a predefined/predetermined threshold or which reaches significant difference from baseline are suggesting that intensity should not exceed the level of this intensity group.

In some embodiments, if no event-related response ERP is found to be significantly different from baseline, there is a basis to assume that the stimulation did not cause any brain activity modification. This could be caused by misplacement or blocking of the actuators (i.e., speakers in the case of auditory stimulation) or subject insensitivity to the stimulation. In both cases, the stimulation can be considered as ineffective and any feedback provided to the user/patient about the stimulation effectiveness (or sleep related parameter) would be inaccurate.

In some embodiments, if no significant difference from baseline was reached for all tested intensities within the interval from perceived intensity to safety standard level, a warning is sent to user interface 160 of system 100. In some embodiments, this warning could be directly communicated to the user or used to adjust any sleep parameter (e.g., estimated or calculated) that may have been affected by stimulation ineffectiveness.

In some embodiments, the emphasis was on sensory stimulation during Non-Rapid Eye Movement (NREM) sleep. However, stimulation can also be applied during REM sleep. In such an embodiment, the procedure described in previous sections can also be applied with the sole difference that stimulation is specifically targeted to be delivered during Rapid-Eye Movement (REM) sleep.

Figure 8:
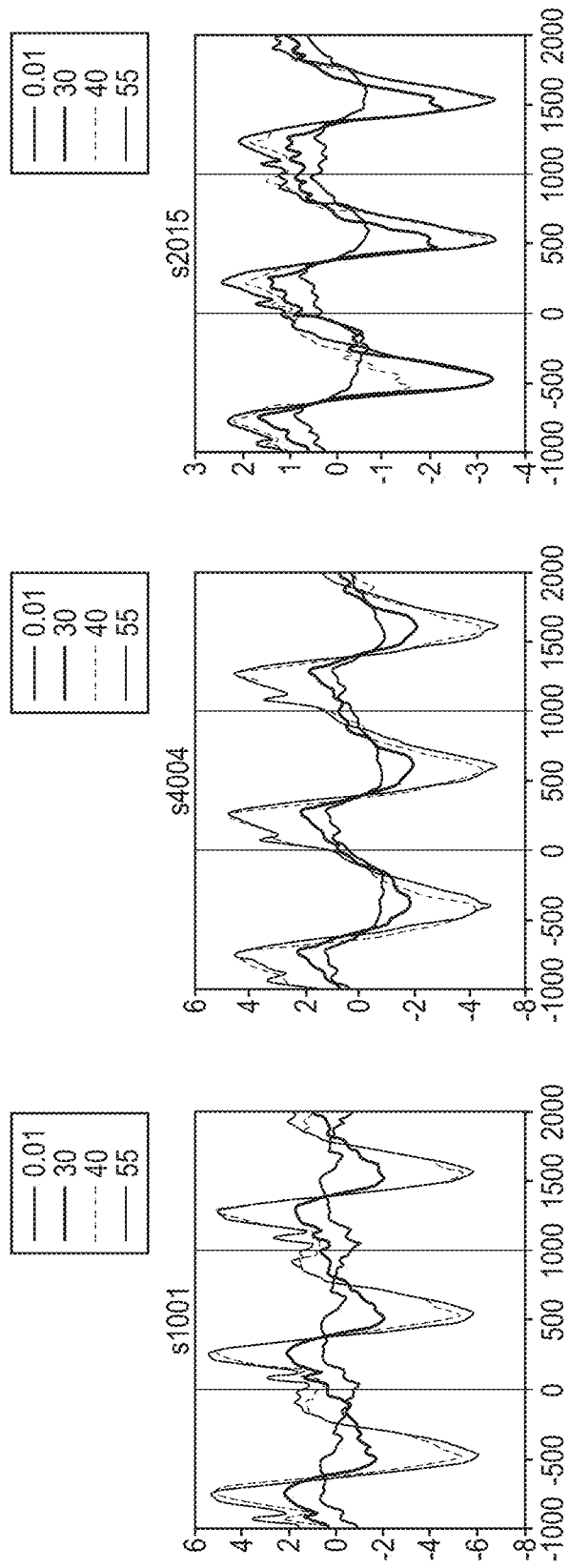
FIG. 8 shows exemplary responses to a tone (e.g., delivered at time 0 and 1000) that is very sensitive to volume and the size of the response at the same volume, however, differs between subjects in accordance with an embodiment of the present patent application.
Figure 8:
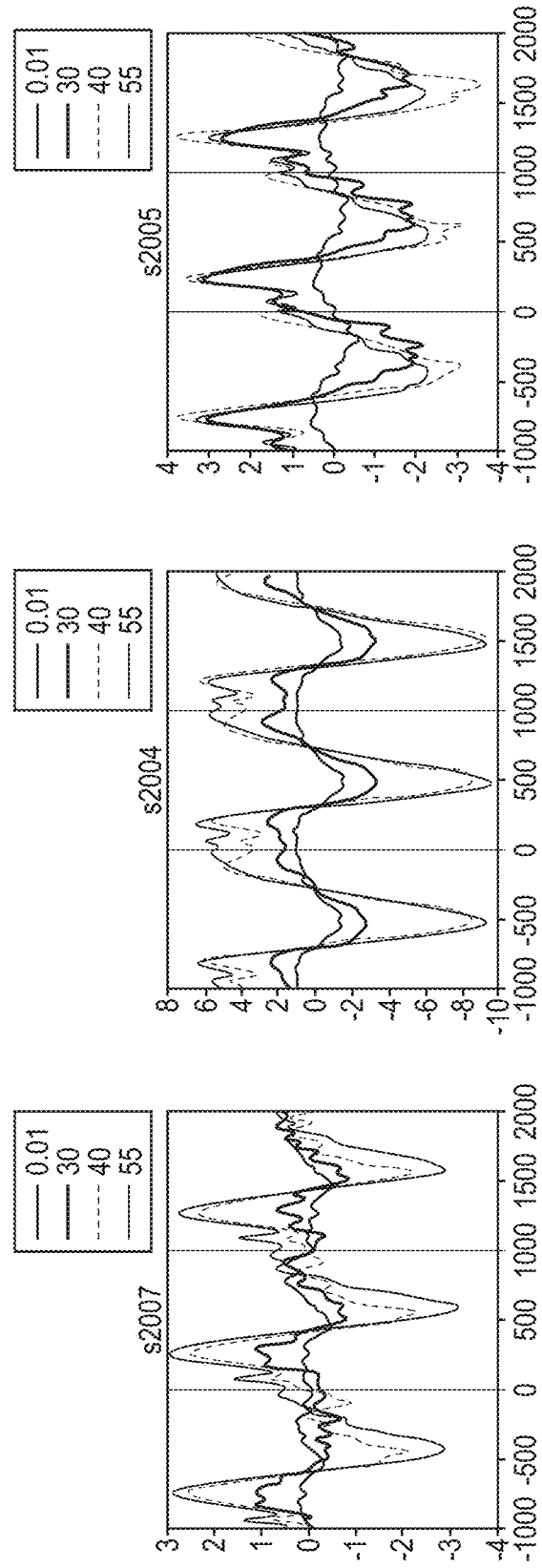

FIG. 8 shows exemplary results across subjects/patients that are pretty consistent. For example, FIG. 8 shows exemplary response to a tone (delivered at time 0 and 1000) is very sensitive to volume (in different colors). In some embodiments, the size of the response at the same volume, however, differs between subjects/patients.

Figure 9:
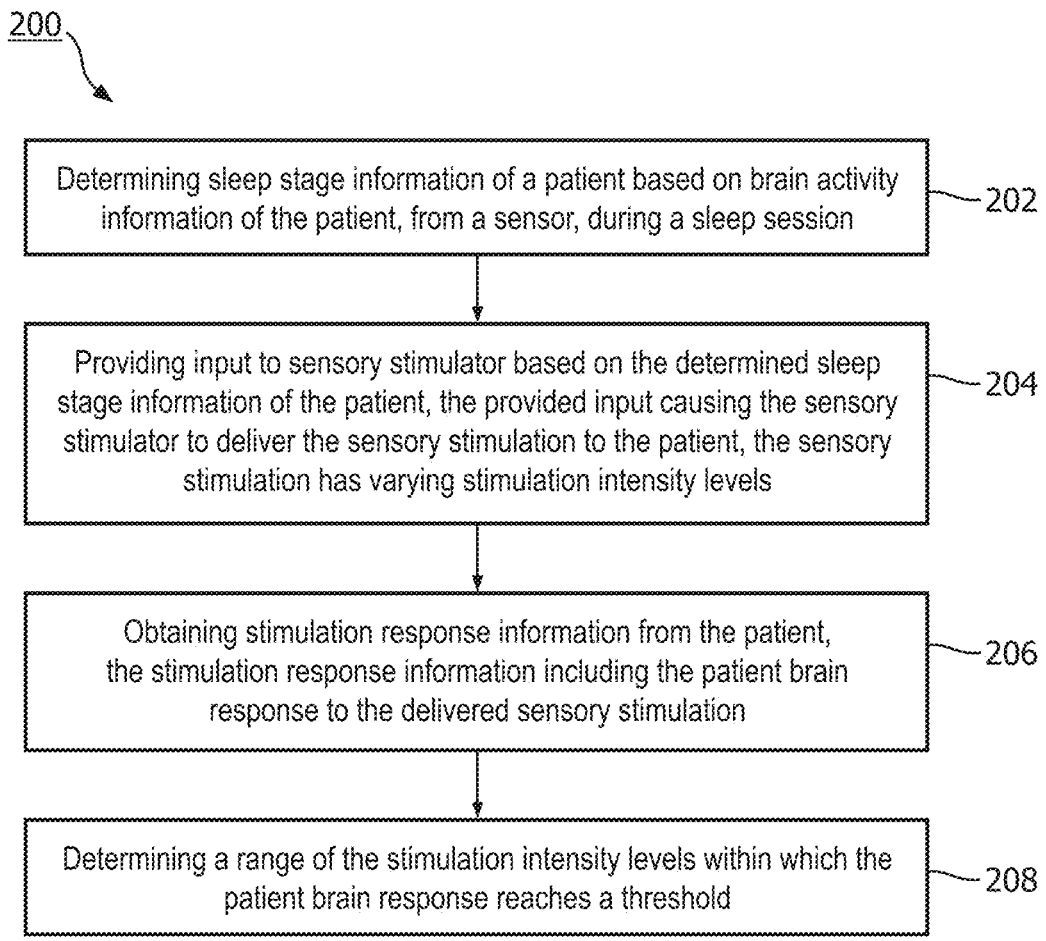
FIG. 9 shows a method for delivering sensory simulation in accordance with an embodiment of the present patent application.

Referring to FIG. 9, a method 200 for delivering sensory stimulation is provided. Method 200 is implemented by computer system 106 that comprises one or more physical/hardware processors 108 executing computer program/machine readable instructions that, when executed, perform method 200. In some embodiments, method 200 comprises determining sleep stage information of a patient based on brain activity information of a patient, from sensor 102, during a sleep session at procedure 202; providing input to sensory stimulator 104 based on the determined sleep stage information of the patient, the provided input causing sensory stimulator 104 to deliver the sensory stimulation to the patient, the sensory stimulation has varying stimulation intensity levels at procedure 204; obtaining stimulation response information from the patient, the stimulation response information including patient brain response to the delivered sensory stimulation at procedure 206; and determining a range of the stimulation intensity levels within which the patient brain response reaches a threshold at procedure 208.

In some embodiments, a subsystem of system 100 is configured to continuously obtain subsequent brain activity information, sleep stage information and stimulation response information. As an example, the subsequent information may comprise additional information corresponding to a subsequent time (after a time corresponding to information that was used to determine a range of stimulation intensity levels). The subsequent information may be utilized to further update or modify the thresholds for the patient brain response, the maximum stimulation intensity level, and the minimum intensity level of the patient (e.g., new information may be used to dynamically update or modify the thresholds for the patient brain response, the maximum stimulation intensity level, and the minimum intensity level), etc. For example, the subsequent information may also be configured to provide further input to determine thresholds for the patient brain response, the maximum stimulation intensity level, and the minimum intensity level. In some embodiments, a subsystem of system 100 may be configured to determine the thresholds for the patient brain response, the maximum stimulation intensity level, and the minimum intensity level and/or to control sensory stimulator 104 to adjust the sensory stimulation to the patient in accordance with a recursively refined profile (e.g., refined through recursive application of profile refinement algorithms) based on previously collected or subsequent information.

In some embodiments, system 100 is configured to obtain input parameters from the patient. In some embodiments, these input parameters may include age (e.g., by means of a one-time questionnaire where the user could input his/her date of birth), mental states (e.g., subjective impression of current/past level of stress), or the result of daytime activity tracking (e.g., the amount and intensity of physical activity).

In some embodiments, the input parameters are input by the patient (or caregiver) into computer system 106 using user interface 160. In some embodiments, computer system 106 may include patient input parameter information subsystem for further processing this information. In some embodiments, system 100 is configured to receive patient input parameter information to determine a range of stimulation intensity levels within which the patient brain response reaches a threshold using the patient input parameter information. In some embodiments, system 100 is configured to adapt some of its system parameters based on the obtain input parameters from the patient. In some embodiments, the system parameters include the threshold.

Figure 2:
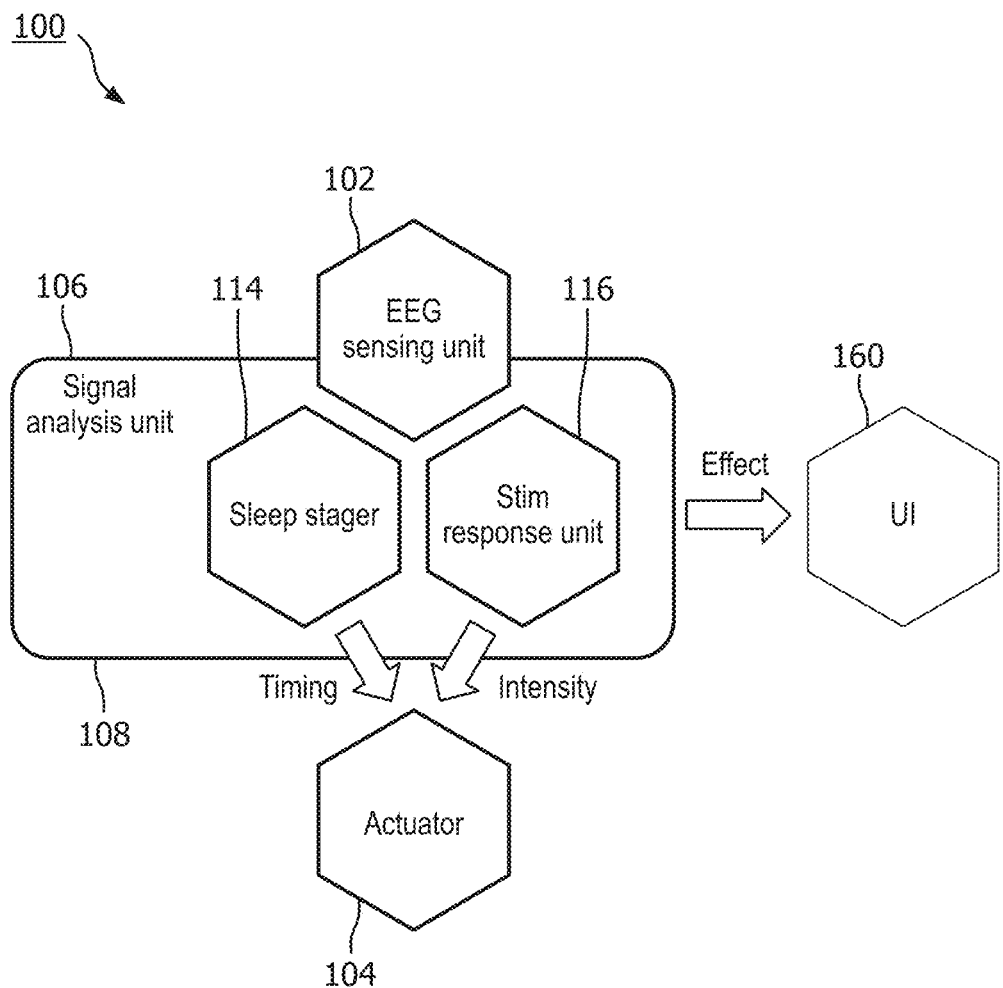
FIG. 2 shows an exemplary system for delivering sensory simulation in accordance with an embodiment of the present patent application.

In some embodiments, the various computers and subsystems illustrated in FIGS. 2 and 3 may comprise one or more computing devices that are programmed to perform the functions described herein. The computing devices may include one or more electronic storages (e.g., database 132, or other electronic storages), one or more physical processors programmed with one or more computer program instructions, and/or other components. The computing devices may include communication lines or ports to enable the exchange of information with a network (e.g., network 150) or other computing platforms via wired or wireless techniques (e.g., Ethernet, fiber optics, coaxial cable, WiFi, Bluetooth, near field communication, or other communication technologies). The computing devices may include a plurality of hardware, software, and/or firmware components operating together to provide the functionality attributed herein to the servers. For example, the computing devices may be implemented by a cloud of computing platforms operating together as the computing devices.

The electronic storages may comprise non-transitory storage media that electronically stores information. The electronic storage media of the electronic storages may include one or both of system storage that is provided integrally (e.g., substantially non-removable) with the servers or removable storage that is removably connectable to the servers via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information received from the servers, information received from client computing platforms, or other information that enables the servers to function as described herein.

The processors may be programmed to provide information processing capabilities in the servers. As such, the processors may include one or more of a digital processor, an analog processor, or a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 112-120 or other subsystems. The processors may be programmed to execute computer program instructions by software; hardware; firmware; some combination of software, hardware, or firmware; and/or other mechanisms for configuring processing capabilities on the processors. In some embodiments, hardware processors may be interchangeably referred to as physical processors. In some embodiments, machine readable instructions may be interchangeably referred to as computer program instructions.

It should be appreciated that the description of the functionality provided by the different subsystems 112-120 described herein is for illustrative purposes, and is not intended to be limiting, as any of subsystems 112-120 may provide more or less functionality than is described. For example, one or more of subsystems 112-120 may be eliminated, and some or all of its functionality may be provided by other ones of subsystems 112-120. As another example, additional subsystems may be programmed to perform some or all of the functionality attributed herein to one of subsystems 112-120.

It should be appreciated that the different subsystems 112-120 performing the operations illustrated in FIGS. 2 and 3 may reside in a system with sensor 102 and sensory stimulator 104. In some embodiments, the different subsystems 112-120 performing the operations illustrated in FIGS. 2 and 3 may reside in an independent monitoring device.

In some embodiments, computer system 106 and/or physical processors/server 108 are included in a smartphone associated with the patient and/or other computing devices. In some embodiments, computer system 106 and/or physical processors/server 108 are included in a tablet computer, a laptop computer, a desktop computer, a server computer, and/or other computing devices. In some embodiments, the smartphone comprises an input configured to receive the information in the output signals generated by sensor 102 and/or other information. The input device may be and/or include a microphone included in the smartphone, a USB input device, an Apple Lightning type connector (which can also provide power), a combined microphone/earphones jack, and/or other devices. In some embodiments, converter devices are configured to convert the output signals, and/or the information in the output signals from sensor 102 for transmission to, and receipt by, the smartphone input device. In some embodiments, computer system 106 and/or physical processors/server 108 are configured such that subsystems 112-120, and/or other subsystems form an electronic application (an "app") running on computer system 106 and/or physical processors/server 108. In some embodiments, the app (as described above related to subsystems 112-120, and/or other subsystems) reads the transformed signal from converter and transmitter devices, converts it back to an EEG signal (if necessary), and analyzes the signal to determine the information described above.

In some embodiments, as shown in FIG. 2, system 100 may include user interface 160 be configured to provide an interface between system 100 and a user (e.g., a patient or a caregiver, etc.) through which the user can provide information to and receive information from system 100. This enables data, results, and/or instructions and any other communicable items, collectively referred to as "information," to be communicated between the user and system 100. Examples of interface devices suitable for inclusion in user interface include a keypad, buttons, switches, a keyboard, knobs, levers, a display screen, a touch screen, speakers, a microphone, an indicator light, an audible alarm, and a printer. In some embodiments, information may be provided to the patient by the user interface in the form of auditory signals, visual signals, tactile signals, and/or other sensory signals. It is to be understood that other communication techniques, either hard-wired or wireless, are also contemplated herein as the user interface. For example, in some embodiments, the user interface may be integrated with a removable storage interface provided by electronic storage 132. In this example, information is loaded into system 100 from removable storage (e.g., a smart card, a flash drive, a removable disk, etc.) that enables the user(s) to customize system 100. Other exemplary input devices and techniques adapted for use with system 100 as user interface include, but are not limited to, an RS-232 port, RF link, an IR link, modem (telephone, cable, Ethernet, internet or other). In short, any technique for communicating information with system 100 is contemplated as the user interface.

In some embodiments, system 100 may also include a communication interface that is configured to send input/control signals to sensory stimulator 104 based on the determined parasympathetic nervous system information through an appropriate wireless communication method (e.g., Wi-Fi, Bluetooth, internet, etc.). In some embodiments, system 100 may include a recursive tuning subsystem that is configured to recursively tune its intelligent decision making subsystem using available data or information to provide better overall adjustment of sensory stimulator 104 and/or better overall control of sensory stimulator 104. In some embodiments, intelligent decision making subsystem, communication interface and recursive tuning subsystem may be part of computer system 106 (comprising server 108).

In some embodiments, the present patent application includes or covers any system in which sleep recordings could be used, the amplitude of the signal is progressively changed by simply multiplying the input signal by a factor with small steps, and the resulting volumes are measured. In such a system, a change of volume boundaries will be observed as a result of the intervention. In some embodiments, an exemplary signal simulator may include SIGGI 2 (http://brainvision.co.uk/easycap-siggi-ii). To make it even more precise, SWs in the existing recordings can be detected and only the amplitude of those instead of the whole signal can be modulated. In both cases, volume boundary changes will result. In some embodiments, in such a system, data/information/signals that are used for the sensory stimulation together with the EEG signals over a number of nights and/or subjects are recorded. In some embodiments, in such a system, subject specific stimulation intensity boundaries and correlation of the stimulation intensity limits with the amplitude of a number of known even-related features can be determined. Artificial signals simulating amplitude differences in a short interval after tone onset at different intensity levels can be used in such a system.

In some embodiments, system 100 is used with any sleep devices/systems, any sleep portfolios, any sleep solutions that are known to one skilled in the art. In some embodiments, system 100 is used in a clinical setting sleep devices/systems. In some embodiments, system 100 is used in a home setting sleep devices/systems. In some embodiments, a mobile application can be part of the health suite digital platform.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the present patent application has been described in detail for the purpose of illustration based on what is currently considered to be the most practical and preferred embodiments, it is to be understood that such detail is solely for that purpose and that the present patent application is not limited to the disclosed embodiments, but, on the contrary, is intended to cover modifications and equivalent arrangements that are within the spirit and scope of the appended claims. For example, it is to be understood that the present patent application contemplates that, to the extent possible, one or more features of any embodiment can be combined with one or more features of any other embodiment.

What is claimed is:

1. A system for delivering modulated sensory stimulation having varying stimulation intensity levels to a patient, comprising:

a sensor configured to measure brain activity information of a-the patient during a sleep session;

a sensory stimulator configured to deliver sensory stimulation to the patient during the sleep session, the sensory stimulation being modulated sensory stimulation having varying stimulation intensity levels; and a computer system that comprises one or more physical processors operatively connected with the sensor and the sensory stimulator, the one or more physical processors being programmed with computer program instructions which, when executed cause the computer system to:

determine sleep stage information of the patient based on the brain activity information of the patient during the sleep session;

cause the sensory stimulator to deliver the modulated sensory stimulation to the patient during the sleep session based on the determined sleep stage information of the patient;

obtain stimulation response information from the patient during the sleep session, the stimulation response information including patient brain response to the delivered modulated sensory stimulation; and determine during the sleep session and based on the stimulation response information a minimum stimulation intensity level and a maximum stimulation intensity level, the minimum stimulation intensity level being a lowest level at which the delivered modulated sensory stimulation elicited a detectable patient brain response to the delivered modulated sensory stimulation and the maximum stimulation intensity level being a saturation level greater than the minimum intensity level at which the brain response of the patient brain response to the delivered modulated sensory stimulation has reached saturation, wherein the saturation level is an intensity level of the delivered modulated stimulation below which the patient brain response to the delivered modulated sensory stimulation changes and above which the patient brain response to the delivered modulated sensory stimulation does not change, and wherein the saturation level is below an intensity level that produces arousals in the patient.

2. The system of claim 1, wherein the stimulation response information includes a waveform, an amplitude of positive and/or negative peaks in the waveform, peak to peak distance in the waveform, an average amplitude of the waveform, latency of a number of successive peaks in the waveform, and an area under the waveform in a predefined interval.

3. The system of claim 1, wherein the modulated sensory stimulation is selected from the group consisting of olfactory stimulation, auditory stimulation, visual stimulation, touch stimulation, taste stimulation, and haptic stimulation.

4. A method for delivering modulated sensory stimulation having varying stimulation intensity levels to a patient, the method being implemented by a computer system that comprises one or more physical processors executing computer program instructions that, when executed, cause the computer system to perform the method, the method comprising:

determining, using the computer system, sleep stage information of the patient based on brain activity information of the patient during a sleep session, the brain activity information of the patient during the sleep session being measured by a sensor;

causing a sensory stimulator to deliver the modulated sensory stimulation to the patient during the sleep session based on the determined sleep stage information of the patient;

obtaining stimulation response information from the patient during the sleep session, the stimulation response information including patient brain response to the delivered modulated sensory stimulation; and determining during the sleep session, using the computer system, and based on the stimulation response information a minimum stimulation intensity level and a maximum stimulation intensity level, the minimum stimulation intensity level being a lowest level at which the delivered modulated sensory stimulation elicited a detectable patient brain response to the delivered modulated sensory stimulation and the maximum stimulation intensity level being a saturation level greater than the minimum intensity level at which the patient brain response to the delivered modulated sensory stimulation has reached saturation, wherein the saturation level is an intensity level of the delivered modulated stimulation below which the patient brain response to the delivered modulated sensory stimulation changes and above which the patient brain response to the delivered modulated sensory stimulation does not change, and wherein the saturation level is below an intensity level that produces arousals in the patient.

5. The method of claim 4, wherein the stimulation response information includes a waveform, an amplitude of positive and/or negative peaks in the waveform, peak to peak distance in the waveform, an average amplitude of the waveform, latency of a number of successive peaks in the waveform, and an area under the waveform in a predefined interval.

6. The method of claim 4, wherein the modulated sensory stimulation is selected from the group consisting of olfactory stimulation, auditory stimulation, visual stimulation, touch stimulation, taste stimulation, and haptic stimulation.

7. A system for delivering modulated sensory stimulation having varying stimulation intensity levels to a patient, the system comprising:

means for measuring brain activity information of the patient during a sleep session;

means for delivering the modulated sensory stimulation to the patient during the sleep session; and means for executing machine-readable instructions with at least one processor, which, when executed, cause the system to execute a method the comprising:

determining sleep stage information of the patient based on the brain activity information of the patient during the sleep session;

causing the means for delivering to deliver the modulated sensory stimulation to the patient during the sleep session based on the determined sleep stage information of the patient;

obtaining stimulation response information from the patient during the sleep session, the stimulation response information including patient brain response to the delivered modulated sensory stimulation; and determining during the sleep session and based on the stimulation response information a minimum stimulation intensity level and a maximum stimulation intensity level, the minimum stimulation intensity level being a lowest level at which the delivered modulated sensory stimulation elicited a detectable patient brain response to the delivered modulated sensory stimulation and the maximum stimulation intensity level being a saturation level greater than the minimum intensity level at which the patient brain response to the delivered modulated sensory stimulation reached saturation, wherein the saturation level is an intensity level of the delivered modulated stimulation below which the patient brain response to the delivered modulated sensory stimulation changes and above which the patient brain response to the delivered sensory stimulation does not change, and wherein the saturation level is below an intensity level that produces arousals in the patient.

8. The system of claim 7, wherein the stimulation response information includes a waveform, an amplitude of positive and/or negative peaks in the waveform, peak to peak distance in the waveform, an average amplitude of the waveform, latency of a number of successive peaks in the waveform, and an area under the waveform in a predefined interval.

9. The system of claim 7, wherein the modulated sensory stimulation is selected from the group consisting of olfactory stimulation, auditory stimulation, visual stimulation, touch stimulation, taste stimulation, and haptic stimulation.

* * * * *